United States Patent
Grass et al.

(10) Patent No.: US 6,282,256 B1
(45) Date of Patent: Aug. 28, 2001

(54) COMPUTED TOMOGRAPHY METHOD UTILIZING A CONICAL RADIATION BEAM

(75) Inventors: Michael Grass; Roland Proksa, both of Hamburg (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/400,763

(22) Filed: Sep. 21, 1999

(30) Foreign Application Priority Data

Sep. 24, 1998 (DE) .............................................. 198 43 812

(51) Int. Cl.⁷ ...................................................... A61B 6/03
(52) U.S. Cl. ............................................. 378/15; 378/901
(58) Field of Search ................... 378/4, 15, 901

(56) References Cited

U.S. PATENT DOCUMENTS 5,355,309  * 10/1994  Eberhard et al. ..................... 378/15
5,995,580  * 11/1999  Schaller ................................ 378/15

FOREIGN PATENT DOCUMENTS

2000093422  * 4/2000  (JP) .

OTHER PUBLICATIONS

"Practical Cone Beam Algorithms", by L.A. Feldkamp et al. In Journal of Optical Soc. Am. A, vol. 1, No. 6, pp. 612–619, 1984.

* cited by examiner

Primary Examiner—David V. Bruce
(74) Attorney, Agent, or Firm—John F. Vodopia

(57) ABSTRACT

The invention relates to a computed tomography method where the examination zone is scanned by means of a conical radiation beam. The reconstruction volume can be enlarged by reconstructing the absorption of voxels in a first sub-volume by means of a first reconstruction algorithm and that of voxels in a second sub-volume by means of a second reconstruction algorithm, the assignment of the voxels to the sub-volumes being performed in such a manner that the secondary conditions for the reconstruction algorithms used for these sub-volumes are satisfied.

7 Claims, 6 Drawing Sheets

COMPUTED TOMOGRAPHY METHOD UTILIZING A CONICAL RADIATION BEAM

BACKGROUND OF THE INVENTION

1. Field of the Invention

The invention relates to a computed tomography method which includes the following steps:

generating a conical radiation beam which traverses an examination zone or an object present therein, generating a relative motion, including a rotation about an axis of rotation, between the radiation beam and the examination zone or the object, acquiring, during the relative motion, measuring data which is dependent on the intensity in the radiation beam to the other side of the examination zone, reconstructing the spatial distribution of the absorption within the examination zone from the measuring data acquired by the detector unit.

The invention also relates to a computed tomography apparatus for carrying out the above method.

2. Description of Related Art

A "conical" beam is to be understood to mean a beam of finite dimensions in two mutually perpendicular directions and is detected by a detector unit which is suitable for spatially resolved measurement in these two directions of the intensity of the beam which has been attenuated in the examination zone. A method of this kind is known from a publication by L. A. Feldkamp et al. "Practical Cone Beam Algorithms", Journal of Optical Soc. Am. A, Vol. 1, No. 6/pp. 612–619, 1984.

It is a fundamental drawback of CT methods (CT= computed tomography) utilizing conical radiation beams that some voxels (volume elements) in the examination zone are only temporarily exposed to the radiation during the relative motion between the radiation source and the examination zone and that the absorption in these voxels cannot be reconstructed from the measuring data acquired by the detector unit. The part of the examination zone in which the spatial absorption distribution can be reconstructed, therefore, is always smaller than the part exposed to the radiation.

The known method utilizes a reconstruction algorithm for reconstructing the absorption within the rotationally symmetrical zone which is exposed to radiation during the entire relative motion and is shaped like a disc, the reconstruction in practice being limited to a plane slice within this zone. The known method is based on a circular relative motion.

However, there are also CT methods which involve a helical relative motion. In the case of such methods the absorption is not reconstructed in the voxels which are present in the radiation beam at the beginning or at the end of the relative motion.

Citation of a reference herein, or throughout this specification, is not to be construed as an admission that such reference is prior art to the Applicant's invention of the invention subsequently claimed.

SUMMARY OF THE INVENTION

It is an object of the present invention to enlarge the zone in which the absorption distribution is reconstructed. This object is achieved according to the invention in that the method also includes the following steps for the reconstruction of the spatial distribution of the absorption:

a) defining at least one first and one second sub-volume within the overall volume traversed by the radiation beam, b) reconstructing the spatial distribution of the absorption within the first sub-volume by means of a first reconstruction algorithm, c) reconstructing the spatial distribution of the absorption within the second sub-volume by means of a second reconstruction algorithm which deviates from the first reconstruction algorithm.

The invention is based on the consideration that the known methods always utilize only one reconstruction algorithm for the reconstruction. For each voxel the absorption is then reconstructed by means of the same number of calculation steps of the same kind. Each reconstruction algorithm is subject to given secondary conditions (for example, the condition that all voxels in the volume to be reconstructed have been exposed to radiation during the entire relative motion) which are satisfied only in a part of the overall volume (the first sub-volume). These secondary conditions are adequate but not necessary for the reconstruction, i.e. there are additional voxels which do not satisfy this secondary condition but do satisfy less severe secondary conditions which are also adequate for a reconstruction, utilizing a different reconstruction algorithm, even if the signal-to-noise ratio could then be less attractive. These voxels are situated in another part of the overall volume (the second sub-volume).

The reconstruction zone can thus be enlarged by utilizing a hybrid reconstruction method involving a first reconstruction algorithm in a first sub-volume and a second reconstruction algorithm in a second sub-volume (other than the first sub-volume). The second reconstruction algorithm may include calculation steps of the same kind as the first algorithm, but a different number thereof. The term "different reconstruction algorithm" is to be broadly interpreted in this sense.

This invention includes an embodiment which can be used in the case of a circular trajectory (i.e. a trajectory where the relative motion between the radiation source and the detector unit on the one side and the examination zone on the other side is shaped as a circle). The criterion for assignment to the two sub-volumes is then given by the irradiation angle range (being the angular range covered in the relevant plane by the (parallel) projection of the rays from the radiation source to a voxel in a plane which is perpendicular to the axis of rotation, or is covered by the components of the vectors from the radiation source to the voxel in the plane of rotation of the radiation source). Voxels with an irradiation angle range of 360° (which voxels are exposed to radiation during the entire relative motion) are assigned to the first sub-volume and voxels with an irradiation angle range of at least 180° (but less than 360°) are assigned to the second sub-volume which bounds the first sub-volume to both sides and has sides extending perpendicularly to the axis of rotation.

The reconstruction of the absorption of the voxels in the first sub-volume is then performed by means of a first reconstruction algorithm which utilizes a reconstruction angle range of 360° (the reconstruction angle range is to be understood to mean the angular range covered by the (parallel) projections of the rays, used for the reconstruction, from the radiation source to a voxel in a plane which is perpendicular to the axis of rotation). For example, the algorithm described in the previously mentioned publication can be used as the reconstruction algorithm. For the second sub-volume use can be made of a reconstruction algorithm for which a reconstruction angle range of 180° suffices; as is known, CT methods involving a plane fan-shaped radiation beam also utilize reconstruction algorithms which operate with a reconstruction angle range of only 180°.

This invention includes two alternatives for the reconstruction of the absorption in these voxels. In conformity with a first alternative, measuring data is taken into account only from an irradiation angle range of exactly 180°. In conformity with a second alternative, all measuring data is taken into account which has been determined for rays through the relevant voxel, but the contributions by rays whose projection passes through the voxel from 180° offset directions are weighted in such a manner that their overall weight equals that of a single ray (i.e. a ray for one direction for which no ray occurs in the opposite direction). In this case the reconstruction is equivalent to a reconstruction with a reconstruction angle range of 180°, but a more attractive signal-to-noise ratio is obtained.

When the part of the examination zone that can be reconstructed by means of a circular trajectory does not suffice, the examination zone can be scanned along two adjacently situated circular scanning paths. This invention also includes an embodiment which is suitable for such a case. A (disc-shaped) intermediate zone which constitutes a third sub-volume then exists symmetrically with respect to the two circles along which the relative motion takes place. Whereas the absorption of the voxels in the first and the second sub-volume can be reconstructed in the manner explained with reference to Claim 2, the third sub-volume can be reconstructed, for example by means of an ART method (ART=Algebraic Reconstruction Technique).

This invention also includes an embodiment for a helical relative motion between the examination zone and the radiation source or the detector unit wherein the helical relative motion (17) includes a rotation about an axis of rotation (14) and a displacement in the direction parallel to the axis of rotation, wherein an irradiation angle range of exactly $(2N+1)\pi$ exists for voxels in the examination zone, and having the steps of assigning voxels which are covered by the radiation beam and are situated outside the conical radiation beam at the beginning and at the end of the helical relative motion to a first sub-volume, assigning voxels which are situated within the radiation beam at the beginning or at the end of the helical relative motion to the second sub-volume, and reconstructing the absorption distribution in the two sub-volumes by means of different reconstruction algorithms. German patent application 198 25 296.4 discloses a method of this kind in which an irradiation angle range of exactly $(2n+1)\pi$ is obtained for (a part of) the voxels in the examination zone; therein n is an integer. The absorption in these voxels can be reconstructed by means of the known method. The absorption of voxels which are situated within the radiation beam at the beginning or at the end of the helical relative motion cannot be reconstructed by means of the reconstruction method disclosed in the cited document, because the irradiation angle range for these voxels is smaller than $(2n+1)\pi$. Therefore, the secondary condition for the reconstruction method disclosed in the cited document is not satisfied; however, there are voxels with an irradiation angle range of $\pi$ or more. These voxels are assigned to the second sub-volume and their absorption can be reconstructed by means of the method which is known from PCT/SE 98/000029, provided that each time only the measuring data for an irradiation angle range of exactly 180° is taken into account.

Finally, the invention also includes a computed tomography apparatus for carrying out the method according to the invention. A computer tomography apparatus accordingly to the invention includes a radiation source (S) for emitting a conical radiation beam which traverses an examination zone (13) or an object present therein, a two-dimensional detector unit (16) which is connected to the radiation source and serves for the acquisition of measuring data which is dependent on the intensity in the radiation beam to the other side of the examination zone, a drive device (2, 5) for realizing a relative motion, including a rotation about an axis of rotation (14), between the radiation source (S) and the detector unit (16) on the one side and the examination zone (13), or the object, on the other side, and a reconstruction unit (10) for the reconstruction of the spatial distribution of the absorption within the examination zone (13) from the measuring data acquired by the detector unit (16), characterized in that it performs the following steps for the reconstruction of the spatial distribution of the absorption: defining at least one first and one second sub-volume within the overall volume traversed by the radiation beam, reconstructing the spatial distribution of the absorption within the first sub-volume by means of a first reconstruction algorithm, and reconstructing the spatial distribution of the absorption within the second sub-volume by means of a second reconstruction algorithm which deviates from the first reconstruction algorithm.

BRIEF DESCRIPTION OF THE DRAWINGS

The invention will be described in detail hereinafter with reference to the Figures. Therein.

DETAILED DESCRIPTION OF THE PREFERRED EMBODIMENT

Figure 1:
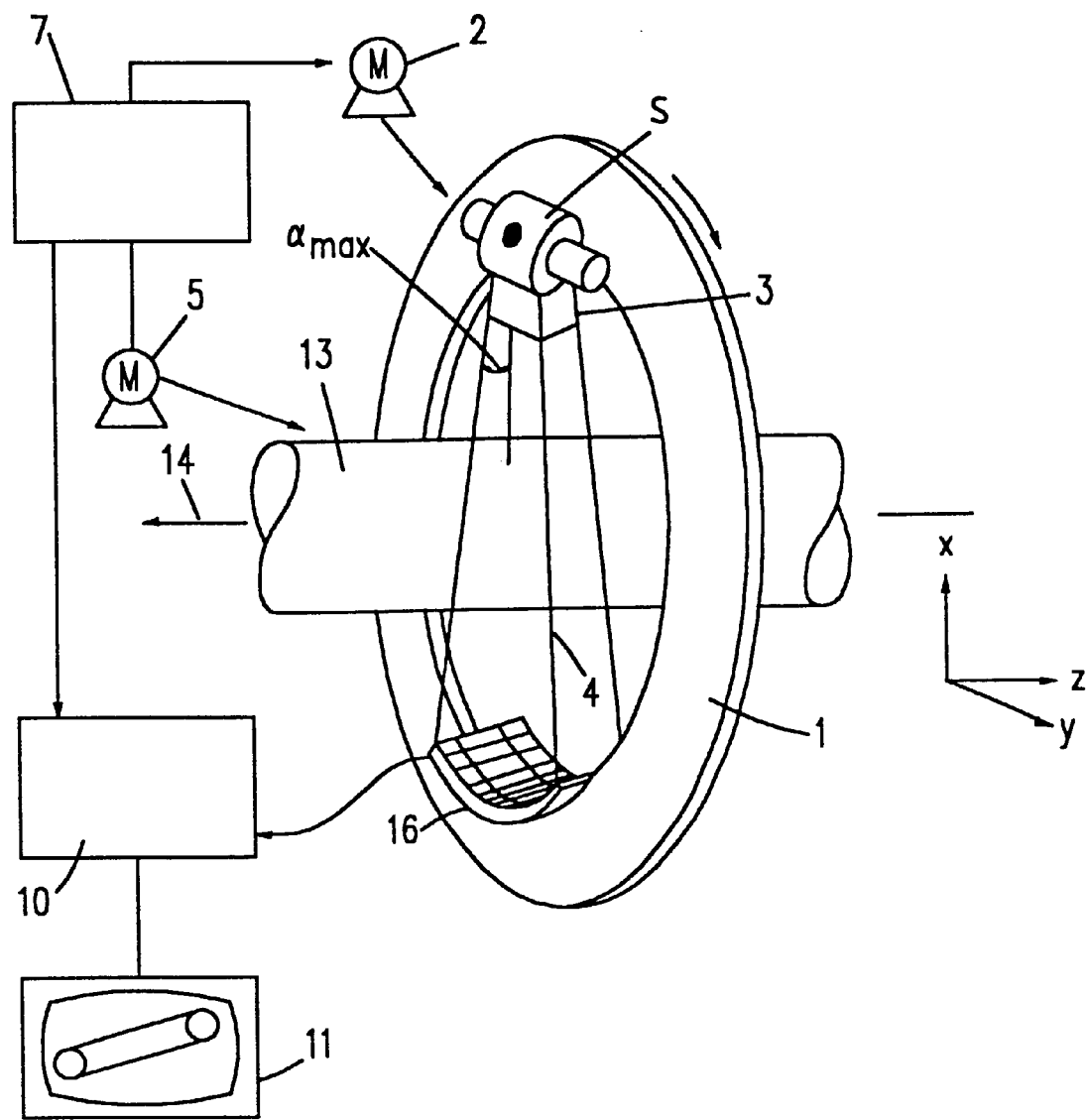
FIG. 1 shows a computed tomography apparatus in which the invention can be carried out.

The computed tomography apparatus shown in FIG. 1 includes a gantry 1 which is capable of rotation about an axis of rotation 14 which extends parallel to the z direction of the co-ordinate system shown in FIG. 1. To this end a motor 2 drives the gantry at a preferably constant but adjustable angular speed. A radiation source S, for example an X-ray source, is connected to the gantry. The source is provided with a collimator device 3 which forms a conical radiation beam 4 from the radiation produced by the radiation source, i.e. a radiation beam which has a finite dimension other than zero in the z direction as well as in a direction perpendicular thereto (i.e. in the x,y plane).

The radiation beam 4 traverses an examination zone 13 in which a patient may be accommodated on a patient table (both not being shown). The examination zone 13 is shaped as a cylinder which will be referred to hereinafter as the object cylinder 13. After having traversed the object cylinder 13, the X-ray beam 4 is incident on a two-dimensional detector unit 16 which is connected to the gantry 1 and comprises a number of detector rows, each of which comprises a plurality of detector elements. Each detector element provides a measuring value for a ray of the radiation beam 4 in each position of the radiation source. The detector unit 16 may be arranged on an arc of circle about the axis of rotation 14, but also on an arc of circle about the radiation source S; however, it may also be plane.

The angle of aperture of the radiation beam 4, denoted by the reference $\alpha_{max}$ (the angle of aperture is defined as the angle enclosed by a ray of the beam 4, situated at the edge in the x,y plane, with respect to a plane of the central ray which is defined by the radiation source S and the axis of rotation 14) then determines the diameter of the object cylinder 13 within which the object to be examined is situated during the acquisition of the measuring values. The examination zone 13, or the object or the patient table, can be displaced parallel to the axis of rotation 14 or to the z axis by means of a motor 5. The transport speed in the z direction is constant and preferably adjustable.

The measuring data acquired by the detector unit is applied to an image processing computer 10 which reconstructs therefrom the absorption distribution in a part of the examination zone 13 and, for example, displays it on a monitor 11. The two motors 2 and 5, the image processing computer 10, the radiation source S and the transfer of the measuring data from the detector unit to the image processing computer 10 are controlled by a suitable control unit 7.

When the motor 5 for the transport in the z direction stands still and the motor 2 rotates the gantry 1, a circular scanning motion is obtained for the radiation source S and the detector unit. The control unit 7, however, can also activate the motors 2 and 5 simultaneously so that the ratio of the displacement speed of the examination zone 13 to the angular speed of the gantry is constant.

Figure 2A:
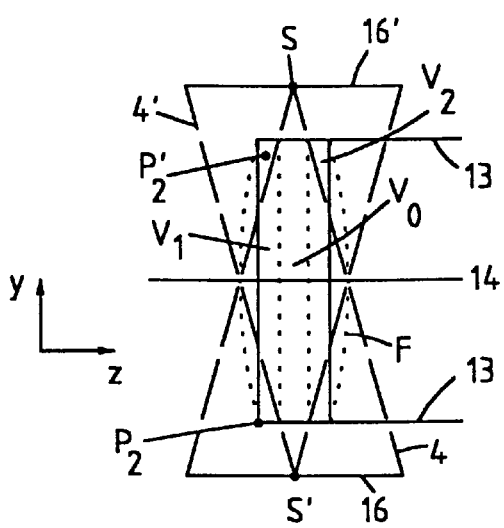
FIGS. 2A–2C show the position of the sub-volumes or individual voxels on the side of a sub-volume, FIG. 3 show a flow chart of a reconstruction method according to the invention.

FIG. 2A shows the radiation source S, being denoted by a dot, the detector unit 16, being symbolized by a line, and the radiation beam 4 in a first position relative to the axis of rotation 14 and in a position which is 180° offset with respect thereto and is denoted by the references S', 16' and 4'. FIG. 2A also shows the examination zone 13. For the sake of clarity the dimensions in the direction parallel to the axis of rotation are shown at a larger scale than those in the direction perpendicular thereto. The absorption in all voxels which are situated within the approximately disc-shaped sub-volume $V_1$ of the examination zone 13 that is covered by the radiation beams 4 and 4' and the radiation beams emitted in all other radiation source positions can be reconstructed by means of the previously mentioned Feldkamp reconstruction algorithm or by means of another reconstruction algorithm for circular trajectories. Because of the unusual shape of this sub-volume, however, reconstruction will be limited to the dotted plane zone which is denoted by the reference $V_0$ in FIG. 2A. It appears that the zone $V_0$ is small in comparison with the part of the examination zone which is traversed by radiation.

FIG. 2A also shows two sides which extend perpendicularly to the axis of rotation and intersect the peak of the sub-volume $V_1$. A voxel on one of the sides and at the edge of the examination zone 13 is denoted by the reference $P_2$.

Figure 2B:
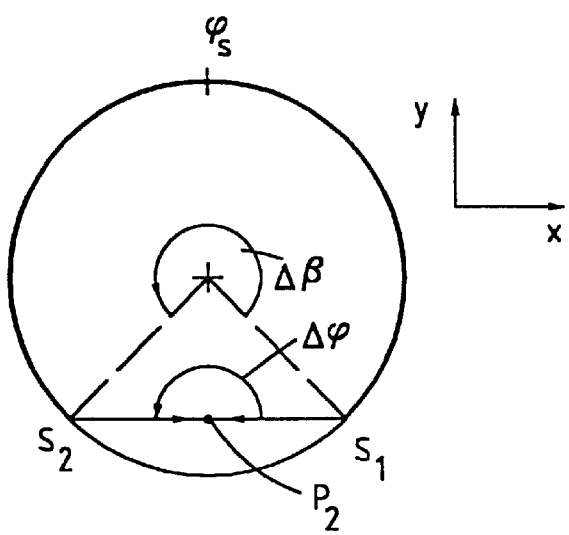

FIG. 2B shows (rotated through 90° relative to FIG. 2A) the circular path along which the radiation source rotates about the axis of rotation 14 as well as the voxel $P_2$ on the side. The part of the circular path wherefrom $P_2$ does not receive radiation because the aperture of the radiation beam is not large enough in the direction of the axis of rotation is shown to be thinner than the part of the path wherefrom the voxel $P_2$ receives radiation. The transitions between the two arcs of circle are denoted by the radiation source positions $S_1$ and $S_2$. It appears that the heavy arc of circle extends symmetrically with respect to an angular position $\psi_s$ in which a ray from the radiation source to the voxel $P_2$ passes exactly through the axis of rotation 14.

FIG. 2B also shows that the radiation source must rotate through an angle $\Delta\beta$ of more than 180° from the position $S_1$ to the position $S_2$, even though the irradiation angle range $\Delta\psi$ (being the angular range covered by the parallel projection of the rays from the radiation source to the voxel $P_2$ on the x-y plane) corresponds to exactly 180°. This difference between $\Delta\beta$ and $\Delta\psi$ is less for voxels which are situated nearer to the axis of rotation 14. It can be demonstrated that all other voxels on the sides (outside $V_1$) which are not situated at the outer edge of the examination zone have an irradiation angle range $\Delta\psi$ of more than 180° but less than 360°.

The irradiation angle range is also larger than 180° and smaller than 360° for the voxels lying between the sides and the outer sides of $V_1$. Because the absorption of voxels with an irradiation angle range of at least 180° can be reconstructed (in the case of CT methods involving a flat, fan-shaped radiation beam it is also possible to utilize reconstruction algorithms which operate with a reconstruction angle range of only 180°), this part of the examination zone (including its sides) is defined as the second sub-volume $V_2$.

Figure 2C:
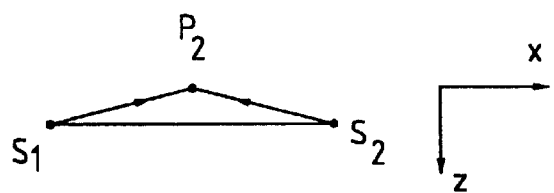

FIG. 2C shows the radiation source positions $S_1$ and $S_2$ in a representation which has been rotated through 90° relative to the FIGS. 2A and 2B. This Figure shows the two rays from the radiation source positions $S_1$ and $S_2$ to the voxel $P_2$ as well as the connecting line between these voxels. An angle which corresponds to the angle of aperture of the conical radiation beam exists between the two connecting lines and the voxel. In the representation of FIG. 2B, in which the two rays are projected onto the x,y plane, this has an effect as if they are offset exactly 180°.

Figure 3:
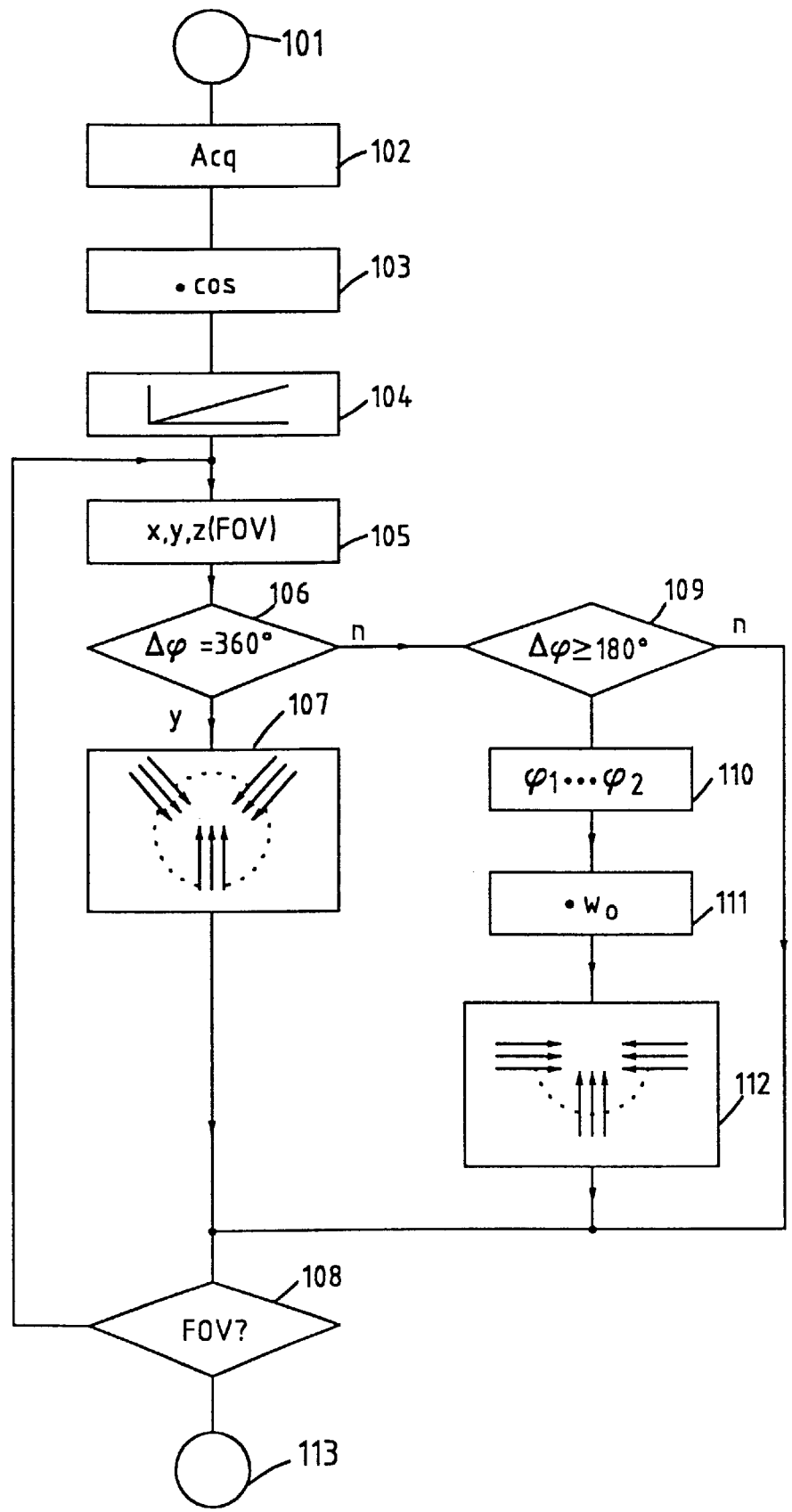

FIG. 3 illustrates the execution of a reconstruction method whereby the absorption distribution can be reconstructed in a significantly larger part of the examination zone.

After initialization in the block 101, the gantry rotates at a constant angular speed. In the step 102 the X-rays are switched on and the measuring data then acquired by the detector unit 16 is stored in a memory of the image processing computer.

During the processing step 103 each measuring value is weighted (multiplied) by a factor which is proportional to the cosine of the angle enclosed by the ray, with which the relevant measuring value is associated, with respect to the central ray (the central ray is the ray which emanates from the radiation source S, intersects the axis of rotation 14 at right angles and is incident at the center of the detector unit 16).

In the step 104 the measuring values supplied by a detector row (situated in the x,y plane) and weighted in conformity with the step 103 are subjected to a high-pass filtering operation. When the detector unit 16 is a plane unit, such filtering is ramp-like, i.e. it has a transfer factor which increases linearly as a function of the spatial frequency. When the detector unit is shaped so as to be curved about the radiation source S or about the axis of rotation 14, it is known that such filtering must be modified.

After all measuring data has thus been processed in conformity with the steps 103 and 104, a voxel x, y, z within a selectable zone (field of view or FOV) is selected (step 105). In the step 106 the flow chart is branched, depending on whether the irradiation angle range $\Delta\psi$ for this voxel is smaller than 360° or not. For a predetermined geometry of the computed tomography apparatus, a look-up table can state, for each voxel in a co-ordinate system connected to the gantry, whether the condition $\Delta\psi=360°$ is satisfied or not.

If the condition is satisfied, i.e. if the relevant voxel has been present in the radiation beam throughout the rotation, the filtered data is backprojected in the step 107, the measuring data from all rays having passed the relevant voxel during the acquisition of the measuring data then being taken into account for this voxel. Each measuring value is then multiplied by a so-called "magnification factor" which is dependent on the distance between this voxel and the relevant radiation source position in which the measuring value has been acquired.

If not one ray passes exactly through the relevant voxel in a radiation source position, a ray (or a filtered measuring value) can be found for this radiation source position by interpolation of the measuring values of a plurality of rays.

After the contributions to the relevant voxel have thus been accumulated for all radiation source positions, it is checked in the step 108 whether all voxels in the region FOV to be reconstructed have been traversed. If this is not the case, the flow chart proceeds to the step 105.

The succession of steps 103 . . . 107 essentially corresponds to the reconstruction algorithm indicated by Feldkamp. However, this algorithm is only suitable for reconstructing the absorption for the voxels which are exposed to radiation in all radiation source positions or lie in the disc-shaped zone $V_1$ which is rotationally symmetrically situated relative to the axis of rotation 14. The hybrid reconstruction method according to the invention, however, enables the reconstruction of the absorption distribution in a larger zone.

When it is certain that the voxel x, y, z is not present in the sub-volume $V_1$, i.e. that it is not struck by radiation in all radiation source positions, it is checked in the step 109 whether an irradiation angle range $\Delta\psi$ of at least 180° exists for the selected voxel (this fact may also be contained in a look-up table). If this is not the case, the absorption in the relevant voxel cannot be exactly reconstructed and the program proceeds to the check 108. However, if the irradiation range $\Delta\psi$ amounts to at least 180°, the absorption in this voxel is also reconstructed by means of the reconstruction algorithm to be described in detail hereinafter.

In the step 110 first the irradiation angle range $\Delta\psi$ is then defined; this range is used for the reconstruction of the absorption in the voxel. It is assumed that the selected voxel x, y, z is situated on the outer sides of the sub-volume $V_2$ and at the edge of the examination zone 13, for example like the voxel $P_2$. In this case there is no other choice than to take into account the entire irradiation angle range $\Delta\psi$ between the radiation source positions $S_1$ for the reconstruction, because it satisfies exactly the condition $\Delta\psi=180°$.

Figure 5A:
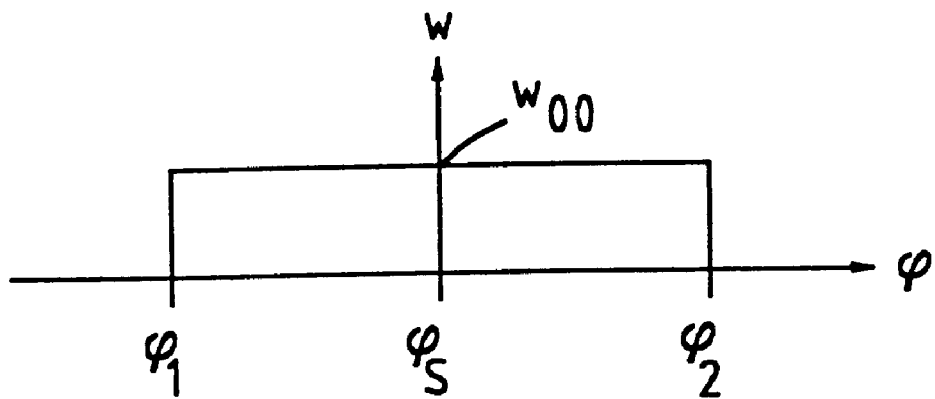
FIGS. 5a and 5b show the weighting factors assigned to the various radiation directions for the reconstruction of the absorption of a voxel.
Figure 5B:
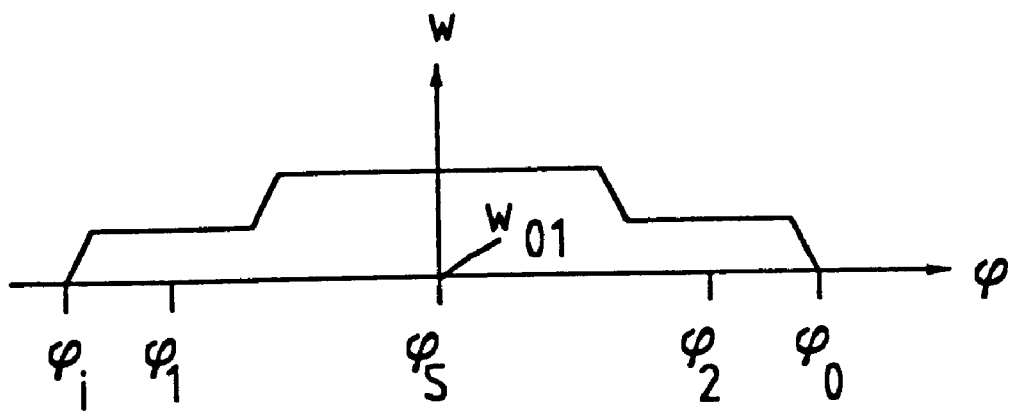

The measuring values of all rays in the irradiation angle range $\Delta\psi$ through this voxel are weighted by a weighting factor $w_0$ in the step 111. In conformity with FIG. 5a, illustrating the dependency of this weighting factor w on the irradiation angle $\psi$, $w_0$ is independent of $\psi$; $\psi_1$ and $\psi_2$ are then the irradiation angles corresponding to the radiation source positions $S_1$ and $S_2$ (in a projection on the x,y plane). The weighting factor $w_0$ is proportional to the value 1/N, where N is the number of radiation source positions on the arc of circle between $S_1$ and $S_2$ (and hence the number of rays passing through the relevant voxel). As a result, the further steps are executed independently of the value N or the angle $\Delta\beta$ completed by the radiation source on the arc of circle from $S_1$ to $S_2$. As has already been described, the angles $\alpha\beta$ and the number N are dependent on the distance between the relevant voxel and the axis of rotation 14.

Backprojection takes place in the step 112; the measuring values of the rays distributed across the irradiation angle range of 180° are then multiplied by the magnification factor which is dependent on the distance between the radiation source position associated with this ray and the voxel. The weighting, being independent of the irradiation angle $\psi$, and the multiplication by the magnification factor, being dependent on the irradiation angle $\psi$, can also be performed in a single step.

Figure 4:
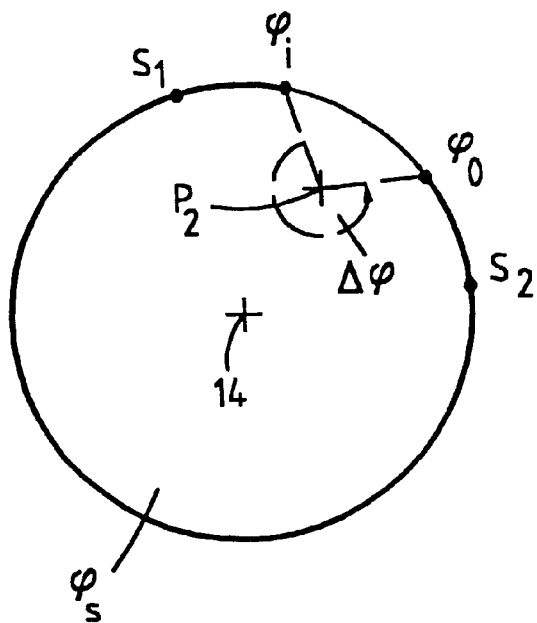
FIG. 4 shows the geometrical conditions for a voxel within the second sub-volume.

When the voxel to be reconstructed is situated within the sub-volume $V_2$ (but outside the sub-volume $V_1$), for example like the voxel $P'_2$ in FIG. 2A, the circumstances are slightly different in comparison with the case where a voxel is situated on the side and at the edge of the examination zone 13 (for example, like $P_2$). This is illustrated on the basis of FIG. 4 which shows the circumstances for the voxel $P'_2$ (see FIG. 2A) in a representation which is analogous to that of FIG. 2B. This figure again shows the angular position $\psi_s$, and $S_1$ and $S_2$ are the radiation source positions which are symmetrically situated with respect thereto and wherefrom the rays to the voxel $P'_2$ (more exactly speaking their projections on the x,y plane) are exactly 180° offset. FIG. 4 shows that to both sides of these radiation source positions there are further positions in the solid region wherefrom the voxel $P'_2$ is irradiated. In this case there are the following possibilities for the steps 110 and 111:

a) A range which corresponds exactly to 180° is cut from the overall irradiation angle range $\psi_i$–$\psi_0$ available, for example a range which is symmetrical relative to the symmetry position $\psi_s$ and is characterized by the radiation source positions $S_1$ and $S_2$ or (see FIG. 5a) by $\psi_1$ and $\psi_2$. The range cut out, however, need not be symmetrical to $\psi_s$. The weighting factor $w_{00}$, with which all measuring values are weighted in the same manner, is then again proportional to the value 1/N.

b) A second possibility consists in taking into account also the rays with an irradiation angle outside the range $\psi_1$ and $\psi_2$ and to weight these rays and a corresponding part of the radiation directions situated between $\psi_1$ and $\psi_2$ in such a manner that the rays through the voxel $P'_2$, whose projections in the x,y plane extend in exactly opposite directions, together are assigned the same weight as, for example the single ray characterized by the radiation angle $\psi_s$ for which no (180° offset) counterpart exists. Because the outer rays are thus taken into account with a weight which is less than that assigned to the rays at the center, this reconstruction is equivalent to a reconstruction with a reconstruction angle range of 180° (FIG. 5a).

The hybrid reconstruction method is terminated after the absorption has thus been determined for all voxels situated in the FOV as well as in the sub-volumes $V_1$ and $V_2$.

Instead of using the Feldkamp algorithm, a different reconstruction algorithm may also be used for the reconstruction of the absorption of the voxels in the sub-volume $V_1$ and $V_2$. Similarly, the absorption distribution in the sub-volume $V_2$ can be reconstructed by means of another reconstruction algorithm enabling the reconstruction from an irradiation angle range of less than 360°.

As is shown in FIG. 2A, the slice which is defined by the sub-volumes $V_1+V_2$ and in which the reconstruction distribution can be reconstructed, is significantly wider than the slice $V_0$ in which the absorption distribution can be reconstructed while utilizing exclusively the Feldkamp algorithm. When an FOV of a diameter smaller than the examination zone 13 is selected, the slice $V_1+V_2$ may even be thicker.

This is because it can be demonstrated that all points within the examination zone with an irradiation angle range $\Delta\psi=180°$ are situated on a convex surface F which is rotationally symmetrical relative to the axis of rotation 14. Such surfaces F, denoted by dashed lines in FIG. 2*a*, are tangent to the apex of the cone. Each slice within the surfaces, but also the volume which is bounded by the surfaces F, can be completely reconstructed. The voxels between the surfaces F and the cone defined by the sub-volume $V_1$ are then assigned to the sub-volume $V_2$ and the voxels inside the cone are assigned to the sub-volume $V_1$.

Figure 6:
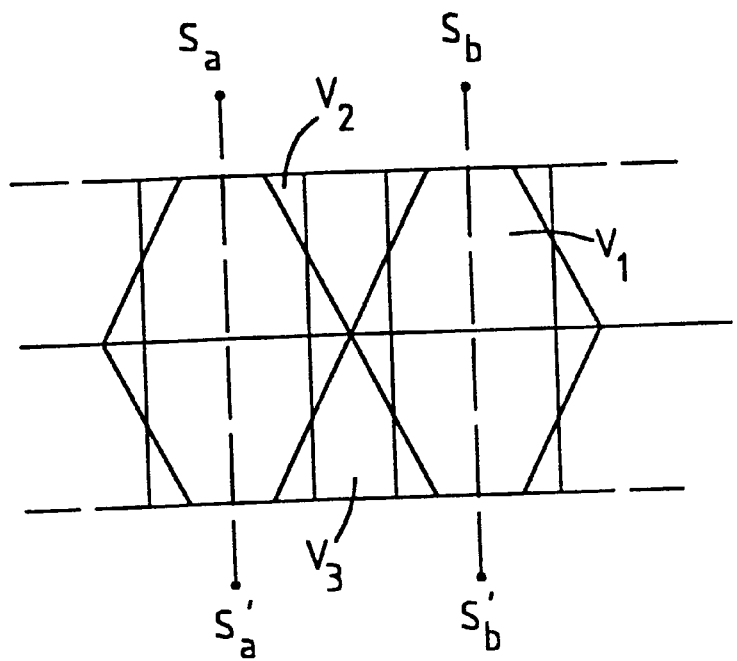
FIG. 6 shows the geometrical conditions in the case of scanning of the examination zone along two mutually offset circular paths.

However, it may occur nevertheless that the overall volumes defined by the surfaces F are not adequate for many applications. In that case the examination zone can be scanned along two circles which are mutually offset in the direction of the axis of rotation. This is illustrated in FIG. 6 in which the references $S_a$ and $S'_a$ denote two 180° offset radiation source positions on the one circle and the references $S_b$ and $S'_b$ denote two 180° offset radiation source positions on the other circle. For reasons of clarity the detector units are not shown, but the resultant sub-volumes $V_1$ and $V_2$ are shown. The reconstruction for the sub-volumes $V_1$ and $V_2$ can again be performed as described with reference to FIG. 3.

Halfway between the circular paths there is situated a flat, slice-like sub-volume $V_3$ which is bounded on both sides by the sides (FIG. 2*a*) belonging to the sub-volume $V_2$. At least the voxels which are situated at the outer edge of the examination zone in the sub-volume have an irradiation angle range of less than 180°.

The assignment to the sub-volumes $V_2$ or $V_1$ again takes place in dependence on the irradiation angle range $\Delta\psi$. The assignment to the sub-volume $V_3$, however, takes place in dependence on the position, i.e. on the z co-ordinate of a voxel.

The reconstruction of the absorption distribution in the volume $V_3$ is effectively performed by means of an ART method. ART methods are iterative methods where the voxels to be reconstructed are first assigned a suitable absorption value, after which the absorption values of voxels situated on the same ray are accumulated and compared with the measuring value acquired for the relevant ray. The difference is suitably distributed between the voxels situated on this ray. After the absorption distribution has thus been corrected in all voxels of the volume to be reconstructed, the described comparison with the acquired measuring data is repeated etc. The ART method enables an approximative reconstruction of the absorption also in the voxels with an irradiation angle range $\Delta\psi<180°$.

The invention can be used not only for CT methods where a circular relative motion takes place, but also for CT methods where a helical relative motion occurs between the examination zone and the radiation source or the detector due to a displacement in the z direction.

Figure 7:
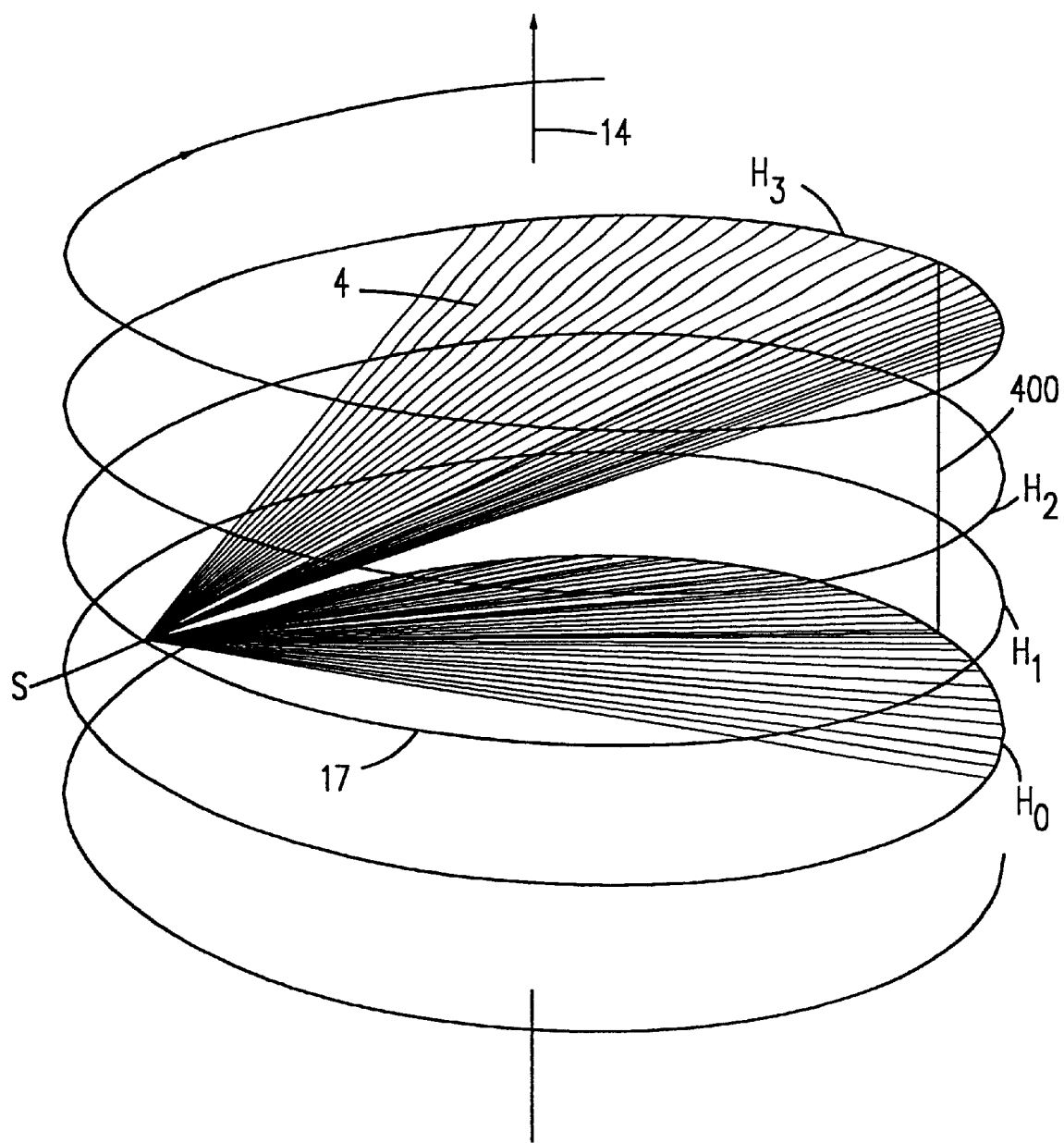
FIG. 7 shows the geometrical conditions in the case of a helical relative motion.

In the case of a helical scanning motion it is in principle irrelevant whether the rotational and displacement motion are performed by the radiation source S and the detector unit 16 or by the examination zone (or the object present therein); only the relative motion is of importance. Therefore, in FIG. 7 it is assumed that the radiation source S (and the detector unit 16 which is connected thereto via the gantry 1 and is not shown in FIG. 7) moves upwards along the helical path 17, whereas the examination zone 13, as well as the object present therein (not shown in FIG. 7), are stationary.

According to a method of this kind which is described in the not previously published German patent application 198 25 296.4, the dimensions of the detector unit, the radiation beam emitted by the radiation source 4, the transport speed and the rotary speed are adapted to one another in such a manner that the detector unit detects exactly the rays which are coincident with the turns $H_0$ and $H_3$ of the helix 17. Because the two helix turns $H_1$ and $H_2$ are also present therebetween, they will be situated at a distance from one another which amounts to three times (generally (2N+1) times) the distance between two neighboring helix turns.

It can be demonstrated that in this case all voxels which enter the radiation beam after the beginning of the scanning of the examination zone and leave this beam before the end of the scanning operation will have been irradiated by the radiation source at an angle of exactly $3\pi$ (generally $(2n+1)\pi$)), thus enabling a very simple reconstruction with a very high image quality.

The foregoing does not hold for the voxels which are already present in radiation beam 4 at the beginning of the scanning motion and the voxels which are still present therein at the end of the scanning motion. The irradiation angle range is smaller for these voxels so that they cannot be reconstructed by means of the method described in the cited document.

However, a hybrid reconstruction can again be performed by assigning all voxels which are situated outside the radiation beam at the beginning and at the end of the helical relative motion to a first sub-volume whose absorption distribution is reconstructed in conformity with the reconstruction algorithm disclosed in the cited document. A part of the voxels that are present in the beam path at the beginning of irradiation, i.e. the voxels projected between the turns $H_1$ and $H_2$ by the radiation source, is irradiated from an angle range of more than 180°. Reconstruction can then be performed by assigning the voxels in this part to a second sub-volume and by reconstructing the absorption distribution therein by means of a method which is known from PCT/SE 98/000029, only the rays for an angle range of exactly 180° then being used for the reconstruction.

The voxels which are projected on the zone between the helix turns $H_0$ and $H_1$ at the beginning of irradiation are irradiated from a range of more than $2\pi$ (but less than $3\pi$). These voxels can be assigned to a third sub-volume whose absorption distribution is reconstructed in that rays from a scanning angle range of 360° are used for each voxel therein.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A computed tomography method comprising:
    generating a conical radiation beam which traverses an examination zone or an object present therein,
    generating a relative motion, including a rotation about an axis of rotation between the radiation beam and the examination zone or the object,
    acquiring, during the relative motion, measuring data which are dependent on the intensity in the radiation beam to the other side of the examination zone,
    reconstructing the spatial distribution of the absorption within the examination zone from the measuring data acquired by the detector unit, wherein the step of reconstructing further comprises:
        defining at least one first and one second sub-volume within the overall volume traversed by the radiation beam,
        reconstructing the spatial distribution of the absorption within the first sub-volume by means of a first reconstruction algorithm, and reconstructing the spatial distribution of the absorption within the second sub-volume by means of a second reconstruction algorithm which deviates from the first reconstruction algorithm.

2. A computed tomography method as claimed in claim 1 wherein the relative motion forms a circle about the axis of rotation, and further comprising:

assigning voxels with an irradiation angle range of 360° to the first sub-volume, assigning voxels with an irradiation angle range of at least 180° but less than 360° to the second sub-volume, reconstructing the absorption of the voxels in the first sub-volume with a reconstruction angle range of 360°, and reconstructing the absorption of the voxels in the second sub-volume in conformity with a reconstruction angle range of 180°.

3. A computed tomography method as claimed in claim 2 further comprising:

defining the 180° offset edge rays of the reconstruction angle range for each voxel in the second sub-volume, and disregarding the contributions by the rays extending through the relevant voxel outside the reconstruction angle range thus defined.

4. A computed tomography method as claimed in claim 2 further comprising:

weighting the contributions by ray pairs which extend through a voxel in the second sub-volume in 180° offset directions in such a manner that their overall weight equals that of a single ray, summing of all, possibly weighted, contributions by rays extending through the relevant voxel, and repeating the steps of weighting and summing for all voxels in the second sub-volume.

5. A computed tomography method as claimed in claim 1 wherein the examination zone is scanned along two circles which are offset in a direction of the axis of rotation, and further comprising:

assigning voxels situated outside a flat intermediate zone which intersects the axis of rotation at right angles, with an irradiation angle range of 360°, to the first sub-volume, assigning voxels situated outside the intermediate zone with a radiation angle range of at least 180° but less than 360° to the second sub-volume, assigning voxels within the intermediate zone to a third sub-volume, and reconstructing the voxels within the third sub-volume by means of an algebraic reconstruction technique (ART) method.

6. A computed tomography method as claimed in claim 1 wherein the relative motion in the form of a helix includes a rotation about an axis of rotation and a displacement in the direction parallel to the axis of rotation, wherein an irradiation angle range of exactly $(2N+1)\pi$ exists for voxels in the examination zone, and further comprising:

assigning voxels which are covered by the radiation beam and are situated outside the conical radiation beam at the beginning and at the end of the helical relative motion to the first sub-volume, p1 assigning voxels which are situated within the radiation beam at the beginning or at the end of the helical relative motion to the second sub-volume, and reconstructing the absorption distribution in the two sub-volumes by means of different reconstruction algorithms.

7. A computed tomography apparatus comprising:

a radiation source for emitting a conical radiation beam which traverses an examination zone or an object present therein, a two-dimensional detector unit which is connected to the radiation source and serves for the acquisition of measuring data which is dependent on the intensity in the radiation beam at the other side of the examination zone, a drive device for realizing a relative motion, including a rotation about an axis of rotation between the radiation source and the detector unit on the one side and the examination zone, or the object, on the other side, and a reconstruction unit for the reconstruction of the spatial distribution of the absorption within the examination zone from the measuring data acquired by the detector unit, wherein the reconstruction unit further comprises means for defining at least one first and one second sub-volume within the overall volume traversed by the radiation beam, reconstructing the spatial distribution of the absorption within the first sub-volume by means of a first reconstruction algorithm, and reconstructing the spatial distribution of the absorption within the second sub-volume by means of a second reconstruction algorithm which deviates from the first reconstruction algorithm.

* * * * *